US00PP35930P2

(12) United States Plant Patent
Bachtell

(10) Patent No.: US PP35,930 P2
(45) Date of Patent: Jul. 2, 2024

(54) ***AMSONIA* PLANT NAMED 'Blue Behemoth'**

(50) Latin Name: ***Amsonia hubrichtii* x *tabernaemontana***
Varietal Denomination: Blue Behemoth

(71) Applicant: Kris Bachtell, Naperville, IL (US)

(72) Inventor: Kris Bachtell, Naperville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 0 days.

(21) Appl. No.: 18/374,554

(22) Filed: Sep. 28, 2023

(51) Int. Cl.
*A01H 5/02* (2018.01)
*A01H 6/08* (2018.01)

(52) U.S. Cl.
USPC ..... Plt./263.1
CPC ..... *A01H 6/08* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Amsonia* plant named 'Blue Behemoth' that is characterized by its upright, dome shaped plant habit, its large plant size, its leaves that are long, narrow and dark in color, its narrow flower petals that are very pale blue in color, and its long (extended) blooming period.

3 Drawing Sheets

Botanical classification: *Amsonia hubrichtii* x *tabernaemontana*.

Cultivar designation: 'Blue Behemoth'.

BACKGROUND OF THE INVENTION

The present invention relates to a new and distinct cultivar of *Amsonia hubrichtii* x *tabernaemontana* plant named 'Blue Behemoth' and will be referred to hereafter by its cultivar name, 'Blue Behemoth'. The new cultivar represents a new herbaceous perennial plant grown for landscape use.

'Blue Behemoth' was discovered as a chance seedling in the Inventor's home garden in Naperville, Illinois in 2005. The parents are unknown. It is believed to be a hybrid between *Amsonia hubrichtii* and *Amsonia tabernaemontana* based on the characteristics of the new cultivar and the presence of plants of the two species in the garden.

Asexual propagation of the new cultivar was first accomplished by division by the Inventor in spring of 2006 in Naperville, Illinois. Asexual propagation by division and stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Blue Behemoth' as a unique cultivar of *Amsonia*.

1. 'Blue Behemoth' exhibits an upright, dome shaped plant habit.
2. 'Blue Behemoth' exhibits a large plant size.
3. 'Blue Behemoth' exhibits leaves that are long, narrow and dark in color.
4. 'Blue Behemoth' exhibits narrow flower petals that are very pale blue in color.

5. 'Blue Behemoth' exhibits a long (extended) blooming period.

'Blue Behemoth' can be compared to *Amsonia hubrichtii* 'String Theory' (U.S. Plant Pat. No. 34,419) and *Amsonia tabernaemontana* 'Fontana' (not patented). 'String Theory' is similar to 'Blue Behemoth' in having abundant narrowly shaped leaves, short internodes, and very pale blue flowers with narrow petals. 'String Theory' differs from 'Blue Behemoth' in having a much smaller plant size, smaller leaves, and a shorter blooming period (ends sooner). 'Fontana' is similar to 'Blue Behemoth' in being densely stemmed. 'Fontana' differs from 'Blue Behemoth' in having a vase-shaped plant habit, a much smaller plant size, wider and shorter leaves, and a shorter blooming period (commences and ends sooner), and flowers that are darker blue in color and smaller in size.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include website listings by Plants Nouveau and The Washington Post.

BRIEF DESCRIPTION OF THE DRAWINGS

The accompanying colored photographs illustrate the overall appearance and distinct characteristics of the new *Amsonia*. The photographs in FIG. 1 and FIG. 2 were taken of 10-year-old plants of 'Blue Behemoth' as grown in a trial garden in Glencoe, Illinois.

The photograph in FIG. 1 provides a view of the plant habit of three plants of 'Blue Behemoth' in peak bloom.

Figure 1:
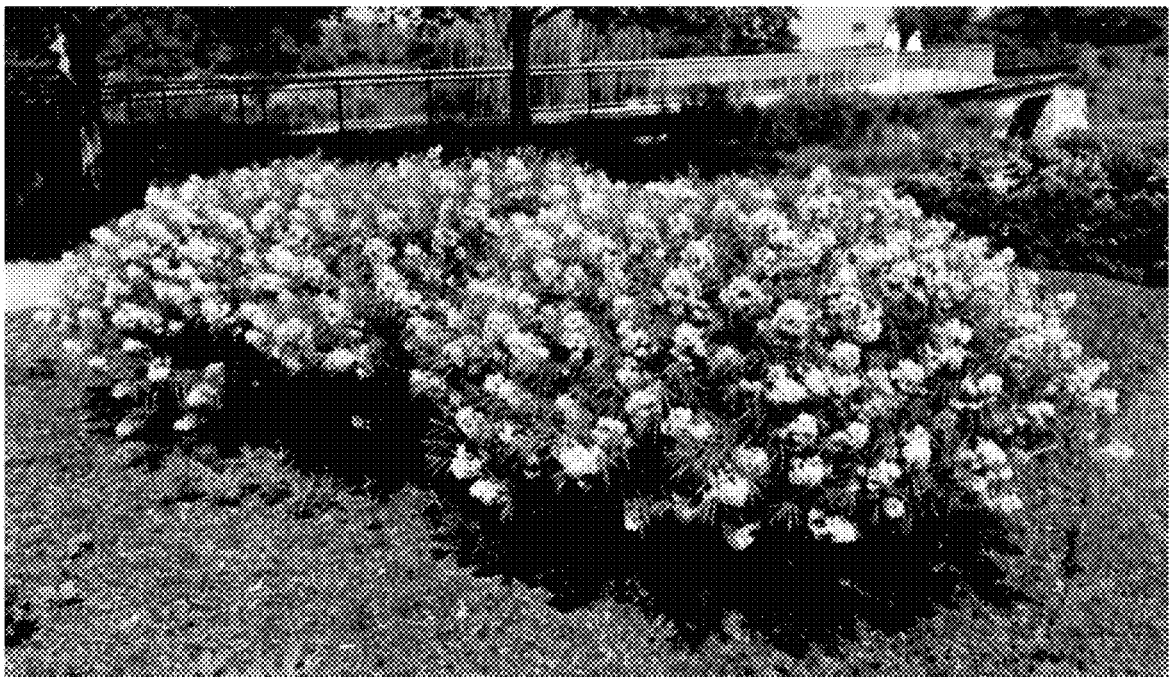
Figure 2:
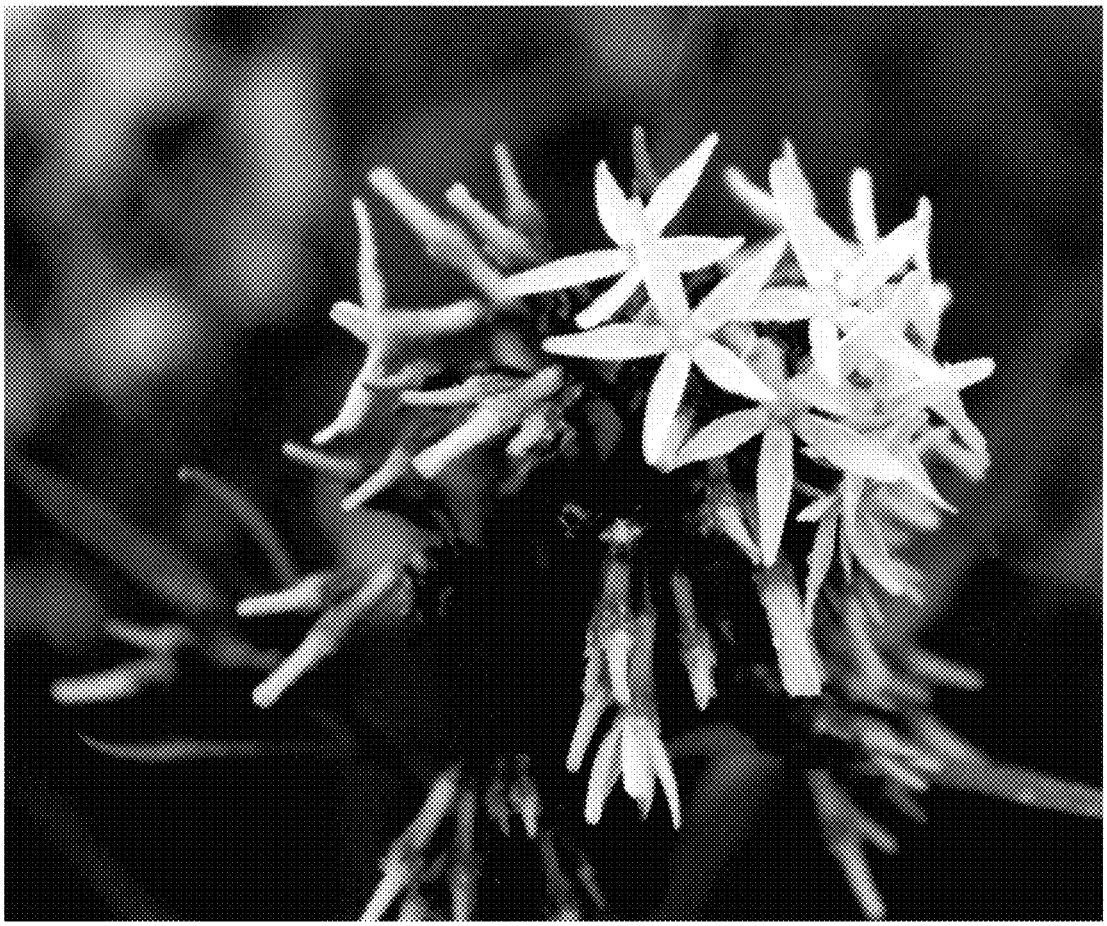

The photograph in FIG. 2 provides a close-up view of an inflorescence of 'Blue Behemoth'.

Figure 3:
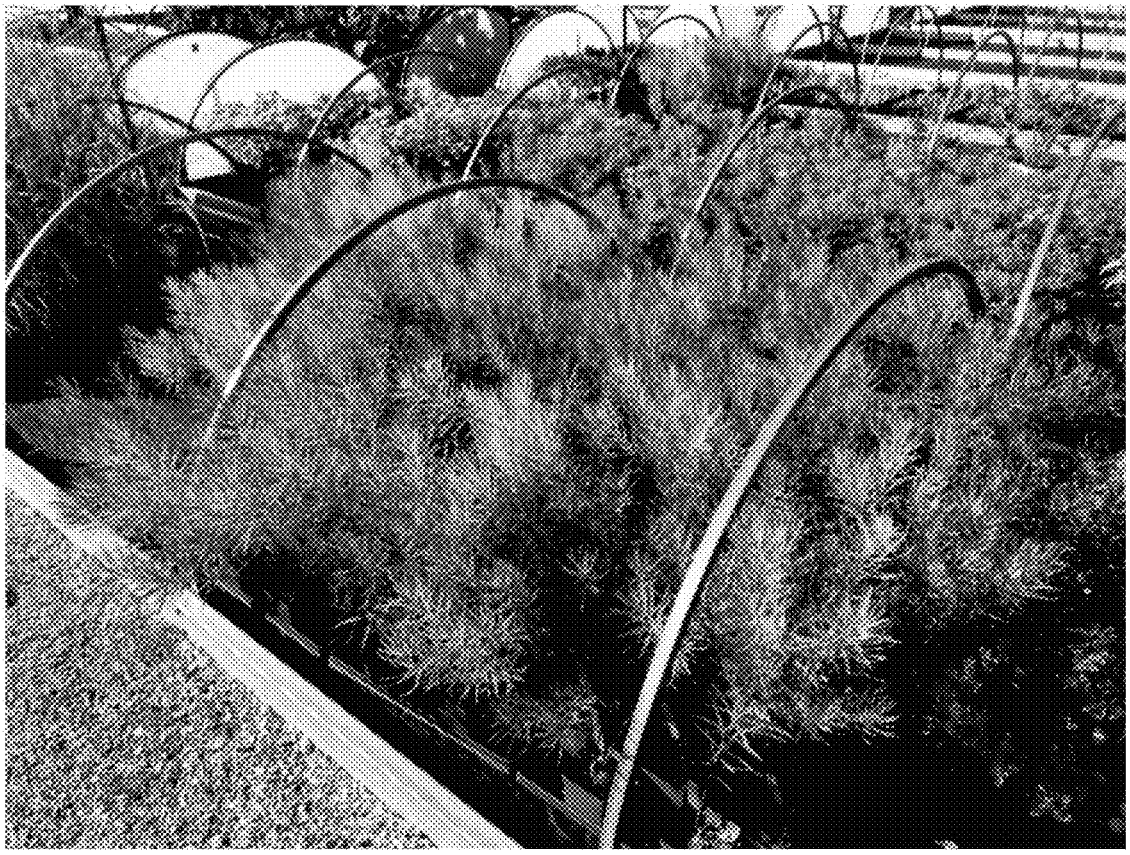

The photograph in FIG. 3 was taken of one-year-old plants of 'Blue Behemoth' as grown in a cold frame in Glencoe, Ilinois.

The colors in the photographs are as close as possible with the photographic and printing technology utilized and the color values cited in the Detailed Botanical Description accurately describe the colors of the new *Amsonia*.

DETAILED BOTANICAL DESCRIPTION OF THE PLANT

The following is a detailed description of one-year-old plants of the new cultivar as grown in 4-inch containers in a cold frame in Glencoe, Illinois. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—6 weeks from mid-May to late June in northern Illinois.

*Plant habit.*—Upright, Dome shaped.

*Height and spread.*—Average of 32 cm in height and 14 cm in width for one-year-old potted plants, mature plants in the landscape reach 1.5 m in height and 2.4 m in width.

*Hardiness.*—At least in U.S.D.A. Zones 4 to 8.

*Diseases and pests.*—No susceptibility or resistance to diseases or pests has been observed.

*Root description.*—Fibrous and fine, color; a blend of 199A, 164A, and 162A.

*Growth rate.*—Vigorous.

*Propagation.*—Cuttings.

*Root development.*—Root initiation occurs in 3 weeks, a young plant from a rooted cutting is produced in about 5 weeks.

Stem description:

*Stem size.*—An average of 30 cm in length and 2 mm in width.

*Stem shape.*—Quadrilateral.

*Stem strength.*—Strong.

*Stem color.*—Base to mid-section 142A, mid-section to top 140A, fall color; a blend of 185A and N34A.

*Stem surface.*—Matte, glabrous.

*Stem aspect.*—Upright.

*Internode length.*—An average of 8 mm.

*Branching habit.*—An average of 5 stems from base, each flowering stem producing a single inflorescence.

Foliage description:

*Leaf shape.*—Linear.

*Leaf division.*—Simple.

*Leaf base.*—Clasping.

*Leaf apex.*—Narrowly acute.

*Leaf venation.*—Parallel, side veins inconspicuous and matches leaf color on upper and lower surfaces, main vein on both surfaces N144D in color, changing in fall; upper and lower surface 7A and 1A, then fading to 158A.

*Leaf margins.*—Entire, strongly rolled inward, no pubescence.

*Leaf attachment.*—Sessile.

*Leaf arrangement.*—Opposite and whorled.

*Leaf surface.*—Both surfaces glabrous, upper surface slightly glossy, lower surface glaucous and matte, main vein glossy.

*Leaf color.*—Young upper and lower surface; N144A, top lightly flushed with 143B, mature upper surface; 141A and sometimes very faintly flushed with 176A, mature lower surface; N138B, older foliage at the base of the stems; upper surface; 151A, slightly mottled with 183A, older foliage at the base of the stems; lower surface; 151A and 152A, center vein flushed with 183A, fall colors; upper and lower surfaces change to a blend of 7A and N30B, and 39A and fade to a blend of 46A and 185A.

*Leaf size.*—Up to 6 cm in length and 4 mm in width.

*Leaf quantity.*—An average of 60 leaves per stem.

*Leaf fragrance.*—None.

Flower description:

*Inflorescence type.*—Panicle on terminus of main stems, one per lateral branch.

*Lastingness of inflorescence.*—About 3 to 4 weeks from the opening of the first flower to senescence of last flower, individual flower lasts about 5 days.

*Inflorescence size.*—An average of 5.5 cm in length and diameter.

*Flower fragrance.*—Light floral scent.

*Flower number.*—An average of 15 open flowers and 64 buds per inflorescence.

*Flower aspect.*—Upright to outward.

*Flower bud.*—Spatulate in shape, acute apex, an average of 1.5 cm in length and 2 mm in width, color; 92B to 92C, calyx portion 141C to 141B, petal portion is glabrous and satiny, center portion is glossy and densely covered with tufts of soft, feathery and fine pubescence, up to 1 mm in length, 92C in color.

*Flower form.*—Salverform.

*Flower size.*—An average of 1 cm in depth, 2.5 cm in width.

*Corolla tube.*—An average of 5 mm in length and 3 mm in width, color; 97B and 98C, outer surface glabrous, glossy, and satiny, inner surface glossy and densely covered with fine, stiff pubescent hairs, up to 1.4 mm in length and N155D in color, the pubescence creates a whirled appearance covering the opening to the corolla tube.

*Corolla lobes.*—5, together making a star-shape, each is linear in shape, held nearly horizontal to slightly cupped when fully open and turning outward as it matures, not overlapping, an average of 1 cm in length and 3 mm in width, apex bifid with a cleft 1 mm in depth and 0.5 mm in width, apex is bluntly acute to rounded, cuneate base fused to tube, entire margins slightly curled upwards, color: when opening both surfaces; 108A and 76D, when fully open both surfaces; 97D and 76D with light flushes of 97A towards the base making faint triangular shapes and on the lower surface as a linear line going down the center.

*Calyx.*—Campanulate in form, comprised of fused sepals with linear shaped sepal tips free, an average of 2 mm in depth and 1 mm in width.

*Sepals.*—5, primarily fused with free tips, linear in shape, entire margins, fused base (about 50%), aristulate apex, an average of 1 mm in length and 0.5 mm in width, inner surface texture; glabrous and shiny, outer surface texture; glabrous and matte, 146A in color.

*Peduncles.*—Round in shape, an average of 1 cm in length and 1 mm in diameter, held outward to slightly pendulous, glabrous and slightly glossy surface, 144A in color.

*Pedicels.*—Round in shape, an average of 3 mm in length and 0.8 mm in diameter, held outward and pendulous, glabrous and slightly glossy surface, 146A in color.

Reproductive organs:

*Gynoecium.*—1 pistil, 4 mm in length; stigma; round and flat, N144A in color, style is 4 mm in length, NN155B in color, ovary; superior, round in shape, about 1 mm in diameter, 144A in color.

*Androecium.*—5 stamens; anthers; dorsifixed, heart-shaped, an average of 1 mm in length, and 200B in color, filaments; fused into petals, an average of 0.4 mm in length and NN155D in color, pollen is high in quantity and 16A in color.

*Fruit and seed.*—Fruit; clusters on plant, up to 8 in a cluster, individual fruits are pod-shaped and linear with a slight bow upwards and outwards, acute shaped tip, flattened attachment, 10 cm in length, 3 mm in diameter, surface is glabrous and glossy, color; young fruit 145A, becomes flushed with 199A, mature fruit turns to a blend of 177A and 200A, when broken the fruit produces a moderate amount of thick white latex, no fragrance, NN155D in color, seeds; cylindrical in shape, apexes are bluntly acute, average of 1.2 cm in length, 2 mm in width, average of 8 seeds per pod, surface is matte and rugose with linear striations, color; a blend of 200B and N199C.

It is claimed:

1. A new and distinct cultivar of *Amsonia* plant named 'Blue Behemoth' as herein illustrated and described.

* * * * *